US 9,393,145 B2

(12) United States Patent
Grunden et al.

(10) Patent No.: US 9,393,145 B2
(45) Date of Patent: Jul. 19, 2016

(54) ANKLE SUPPORT (75) Inventors: Jennifer Grunden, Hamburg (DE);
Birgit Scheib, Hamburg (DE)

(73) Assignee: BSN MEDICAL GMBH, Hamburg (DE)

( * ) Notice: Subject to any disclaimer, the term of this patent is extended or adjusted under 35 U.S.C. 154(b) by 0 days.

(21) Appl. No.: 13/406,813

(22) Filed: Feb. 28, 2012

(65) Prior Publication Data

US 2012/0238929 A1 Sep. 20, 2012

(30) Foreign Application Priority Data

Feb. 28, 2011 (EP) ..................................... 11001626

(51) Int. Cl.
*A61F 5/01* (2006.01)
*A61F 13/06* (2006.01)

(52) U.S. Cl.
CPC ............. *A61F 5/0111* (2013.01); *A61F 5/0104* (2013.01); *A61F 13/066* (2013.01)

(58) Field of Classification Search
CPC .... A61F 5/0104; A61F 5/0111; A61F 13/066
USPC ............... 602/27, 65, 28, 29, 60–62; 128/882
See application file for complete search history.

(56) References Cited

U.S. PATENT DOCUMENTS

| 1,351,248 | A | * | 8/1920 | Hill | ................................. 602/66 |
| 5,067,486 | A | | 11/1991 | Hely | |
| 5,676,641 | A | * | 10/1997 | Arensdorf et al. | ............... 602/27 |
| 5,795,316 | A | | 8/1998 | Gaylord | |
| 6,641,550 | B1 | * | 11/2003 | Johnson | .......................... 602/65 |
| 6,663,583 | B1 | * | 12/2003 | Janis | ............................... 602/65 |
| 7,753,865 | B1 | | 7/2010 | Hely | |
| 8,007,454 | B1 | * | 8/2011 | Zerr | ...................... A61F 5/0111 602/23 |
| 2007/0049856 | A1 | * | 3/2007 | Arensdorf | ........................ 602/27 |
| 2007/0049857 | A1 | | 3/2007 | Quinn et al. | |
| 2009/0076428 | A1 | * | 3/2009 | Kay | .................................. 602/27 |
| 2009/0105704 | A1 | | 4/2009 | Gordon, Jr. | |

OTHER PUBLICATIONS

English Translation of the German Text of the Written Opinion in EP 11 00 1626.8-2310 dated Jul. 29, 2011.

* cited by examiner

*Primary Examiner* — Keri J Nelson
(74) *Attorney, Agent, or Firm* — Shumaker, Loop & Kendrick, LLP (57) ABSTRACT

An ankle brace having a flexible main body that is designed to surround a human leg from the ankle from the lower leg to the midfoot, and having a fixing belt that can be wound around the main body that is affixed, with the first end, to the lateral section of the main body adjacent to its top end, and, with the second end, to the medial section of the main body adjacent to its top end. The ankle brace makes it possible to easily adjust a certain degree of pronation and at the same time be comfortable to wear. One of the first and second end is fixedly or releasably connected to the main body in a fixed position relative to the main body, and that the other of the first and second end is releasably connected to the main body.

12 Claims, 7 Drawing Sheets

ANKLE SUPPORT

TECHNICAL FIELD AND BACKGROUND OF THE INVENTION

The present invention relates to an ankle brace comprising a flexible main body that is designed to surround a human leg in the area of the ankle from the lower leg to the midfoot, wherein the main body comprises a medial section, a lateral section, a sole section having a lateral and medial side, and an arch and instep section, wherein the medial section is provided to contact the medial side, the lateral section is provided to contact the lateral side, the sole section is provided to contact the sole, and the arch and instep section is provided to contact the arch and/or instep of the foot, and having a fixing belt that can be wound around the main body, which has a first end and a second end, wherein the first end of the fixing belt is connected to the lateral section of the main body, and the second end is connected to the medial section of the main body adjacent its top end, and wherein the fixing belt is movably guided around the main body such that the first end of the fixing belt proceeds starting from the lateral section over the arch and instep section to the medial side of the sole section, across the sole section to the lateral side of the sole section, across the arch and instep section, and on to the top end of the medial section.

Ankle braces are used in the field of orthopedic therapy to stabilize and correct the position of the foot relative to the lower leg. The lateral section (pronation) or the medial section (supination) of the foot is frequently lifted to correct this position Ankle braces can be used, for example, to treat torn or sprained ligaments in the ankle.

An ankle brace is known from the prior art, such as U.S. 2007/0049857 on which the present invention is based, in which a fixing belt is firmly connected to the sole section of the main body. Furthermore, the first end of the fixing belt is releasably connected to the lateral section, and its second end is releasably connected to the medial section of the main body adjacent its top end. The releasable connections are created by hook-and-loop fasteners.

A releasable hook-and-loop connection always yields somewhat, however, when the fixing belt is pretensioned, for example, to adjust the pronation or supination. It is impossible to permanently set a precise degree of pronation or supination when the end of the fixing belt opposite the end at which initial tension is introduced is connected to the main body in a yielding manner and not fixedly, and the connection is therefore unable to withstand constant opposing force. Such a connection at both ends of the fixing belt has therefore proven to be disadvantageous.

Furthermore, the fixing belt cannot be completely released from the main body, which can cause unnecessary difficulty or effort for the user the next time the ankle brace is put on.

The fact that the fixing belt is permanently attached to the sole section of the main body is disadvantageous in that the fixing belt cannot be moved freely along the sole section to search for an individual optimum position. In addition, the fact that the fixing belt is permanently connected to the sole section causes the main body to twist or shift relative to the foot surrounded by the main body when the initial tension applied to the first and second end is not equivalent. Pronation or supination cannot be effectively adjusted. In addition, the user must adjust the initial tension at two ends of the fixing belt and adjust them in relation to each other, if necessary, which makes putting on the ankle brace complicated.

From all of the above, it is clear that the brace according to U.S. 2007/0049857 can immobilize the foot joint but cannot correct the position of the bones relative to each other.

An ankle brace is also known from U.S. Pat. No. 5,067,486 with two fixing belts that are attached in the heel area of a main body, wherein the first belt initially proceeds along the lateral section of the main body, then over the arch to the medial side and below the sole section, and finally is releasably attached to the lateral side. The second belt proceeds across the medial section, then over the arch to the lateral side, and finally below the sole section back to the medial side to which it can also be releasably attached.

The position of the bones in the area of the ankle also cannot be corrected with this brace; the ankle can also only be immobilized. In this case as well, the pronation or supination cannot be adjusted by the path of the belt.

Starting from the prior art, it is therefore the object of the present invention to provide an ankle brace that makes it possible to set a precise degree of pronation or supination in a particularly simple way and thereby be very comfortable to wear.

SUMMARY OF THE INVENTION

This object is achieved in that one of the first or second ends is fixedly or releasably connected in a preset position relative to the main body, and that the other of the first or second ends is releasably connected to the main body.

If the ankle brace is to be used to adjust pronation, the first end of the fixing belt is fixedly connected to the lateral section of the main body, and the second end is releasably connected to the medial section of the main body. The releasable connection can, for example, be created by a hook-and-loop fastener.

Alternately, the first end of the fixing belt can be releasably connected to the main body in a preset position relative to the main body. This releasable connection at a preset position can, for example, be created by means of one or more press closures. Press closures are rigid connecting elements that do not yield when initial tension acts on the fixing belt. Consequently, a precise degree of pronation or supination can also be set with this connection.

This releasable connection at a preset position, which can be created by means of one or more press closures as discussed above, can also be described as being created by one or more pushbutton connections. Whether the term pushbutton connection or press closure is used, the term describes such a releasable connection at a preset position such that a precise degree of pronation or supination can be set via the connection.

In the event that the ankle brace is to be used to adjust supination, the second end of the fixing belt is fixedly connected to the medial section of the main body, or alternately releasably connected in a preset position relative to the main body, for example via a snap fastener, and its first end is releasably connected to the lateral section of the main body, for example via a hook-and-loop fastener.

The fixing belt is only connected to the main body in the area adjacent the top end of the main body. The fixing belt proceeds around the sole section without being connected to the main body; rather, it only lies against it and is shiftable in relation thereto. Consequently, the fixing belt can be slid along the sole section when adjusting the degree of pronation or supination without twisting the main body of the brace.

If a user, for example, wants to adjust pronation and thereby tighten the second end of the fixing belt according to the invention, the main body with the foot surrounded by the main body is increasingly lifted with respect to the lateral side of the sole section. An even and effective pronation of the foot is achieved, and the desired degree of pronation can be adjusted by correspondingly pulling the second end of the fixing belt.

In addition, the fixing belt is preferably made of a material that is substantially non-elastic in the longitudinal direction of the belt to prevent the belt from stretching and to also permanently set the degree of pronation or supination.

To attach the fixing belt and thereby set a certain degree of pronation, the second end of the fixing belt can be releasably connected to the area of the medial section of the main body adjacent the top end of the main body with the assistance of a hook-and-loop fastener, preferably Velcro®. To be able to select different adjustment levels and hence different degrees of pronation, the hook-and-loop fastener can be designed wide enough for the second end of the fixing belt to be connectable to the main body at a plurality of locations at a distance from each other in the direction of extension of the fixing belt.

The fixing belt preferably surrounds the main body like a loop in a substantially symmetrical arrangement such that the fixing belt encircles the sole section in the area of the midfoot, crosses itself in the area of the arch and instep, and its two ends are finally attached at the area of the lateral and medial section of the main body adjacent the top end of the main body.

In a preferred embodiment, one end is fixedly connected to the main body. This allows a precise degree of pronation to be set. In addition, it makes it easier for the user to put on the fixing belt.

In another preferred embodiment, one end is releasably connected to the main body in a plurality of preset positions relative thereto. It is particularly preferable when one end is connected to the main body by means of one or more snap fastener connections. This allows a precise degree of pronation to be set, and the fixing belt can also be completely removed from the ankle brace, for example to be replaced. At the same time, the position of the fixed connection can also be adapted to the individual needs of the user. Snap fasteners are a suitable, releasable, but also fixed connecting element.

In another preferred embodiment, the other end is releasably connected to the main body by means of a hook-and-loop connection. A hook-and-loop connection can be quickly and easily opened and closed, and allows fixation to a position that is continuously changeable within a certain range. In this manner, a precise, individually desired degree of pronation or supination can be set.

Because one end is fixedly connected to the main body or releasably connected in a preset position, and the other end is releasably connected, the user also directly perceives the sequence in which the ends have to be attached to the main body, that is, how the fixing belt needs to be tightened. This ensures that the user actually adjusts the pronation or supination as specified and does not for example tighten the fixing belt in the wrong direction.

In yet another preferred embodiment, the main body has guide tabs along the path of the fixing belt to movably guide the fixing belt. The fixing belt can be movably fixed into position along its desired path with such guide tabs. The guide tabs make it easier to use the ankle brace and to ensure a precise and reproducible arrangement of the fixing belt, and are preferably provided on the main body in the area of the arch and instep.

In another preferred embodiment, a lateral splint element is affixed to the lateral section of the main body, and a medial splint element is affixed to the medial section of the main body. The splint elements are for splinting, i.e., strongly reinforcing the area between the lower leg and ankle. They lie against the lower leg on opposite sides.

In another preferred embodiment, an applied reinforcement is provided on the main body and is designed contiguously and extends from the top end of the lateral section and across it, across the sole section, and across the medial section up to its top end. The applied reinforcement can serve to hold the splint elements in a suitable position. Another effect of the applied reinforcement is that it reinforces the sole section and ensures that the lateral and medial sections are held together.

It is particularly advantageous when the material of the applied reinforcement is designed to be nonstretchable in its path from the top end of the lateral section to the top end of the medial section. A preferably anisotropic material that is nonstretchable in one direction such as a fiber-reinforced plastic can be used for the applied reinforcement to prevent the sole section from expanding in the direction between its lateral and medial side and thus to retain the shape of the ankle brace.

It is also particularly preferable when the lateral and medial splint elements are attached between the main body and an applied reinforcement. In this manner, the applied reinforcement can retain the splint elements at the desired location without the splint elements having to be separately attached.

According to a preferred exemplary embodiment that can, of course, also be inventive and hence can also be generally used for an ankle brace having a flexible main body without the aforementioned belt guidance, the main body has a posterior section that is provided to lie on the posterior side of the foot, a lateral ankle section that is provided on the lateral side of the foot to lie on the ankle, and a medial ankle section that is provided on the medial side of the foot to lie on the ankle, wherein the lateral splint element on the lateral section of the main body proceeds offset away from the posterior section such that the lateral splint element proceeds offset from the lateral ankle section toward the arch and instep section, and wherein the medial splint element on the medial section of the main body is arranged offset to the posterior section such that the medial splint element proceeds offset from the medial ankle section toward the posterior section.

The general independent concept of the main body of the ankle brace can be designed to enable entry from the rear, that is, through an opening in the posterior section, as well as from the front, through an entrance area in the arch and instep section.

By arranging the splint elements offset from the ankle sections, the brace prevents a so-called talus prolapse, that is, a forward shift of the ankle bone in relation to the tibia joint surface. Force is exerted on the ankle bone by the offset position of the splint elements when the ankle bone shifts forward in relation to the tibia joint surface.

Another advantage of this arrangement of the splint elements is that they do not lie directly on the ankle which can easily cause pain to the user when pressure is exerted on the splint elements.

In another preferred embodiment, a compression belt made of an elastic material is provided, which has a first and second end, the compression belt being wound around the main body, fixing belt, and applied reinforcement, wherein the first end of the compression belt is fixedly connected to the main body, fixing belt, or applied reinforcement, and the second end of the compression belt is releasably connected thereto.

Compression of the lower extremities in the area of the ankle joint is achieved with a compression belt in addition to correcting (pronation or supination) with the fixing belt and, if applicable, splinting with the splint elements. The compression belt consequently has a similar effect as a bandage. In addition, the compression belt ensures that the splint elements arranged underneath lie closely and rigidly against the tibia bone, tendons, and ligaments and exert a corrective function. The desired degree of compression can be set by tightening the compression belt.

It is particularly preferable when the first end of the compression belt is fixedly attached to the posterior section, when the compression belt is designed to proceed from the posterior section across the lateral section to the lateral side of the sole section, across the sole section to its medial side, across the medial section and arch and instep section of the lateral section, across the lateral section, posterior section and medial section, upward to the area of the lateral section that adjoins the top end of the lateral section, and when the second end of the compression belt is releasably connected in the area of the lateral section that adjoins the top end of the lateral section.

By guiding the compression belt along the main body, applied reinforcement, and fixing belt, the pressure that is applied by tightening the compression belt is very evenly distributed to the structure lying underneath (main body, applied reinforcement, and fixing belt). Unpleasant or orthopedically disadvantaged pressure peaks do not occur.

The second end of the compression belt can be releasably connected to the lateral section by a hook-and-loop fastener or by a Velcro® connection. To releasably connect the second end of the compression belt, a hook-and-loop fastener base can be provided in the area of the lateral section that adjoins the top end of the main body, preferably on the applied reinforcement, dimensioned to allow the second end of the compression belt to be attached at different points of the hook-and-loop fastener base at certain distances from each other in the direction of extension of the compression belt to thereby adjust the set degree of compression.

In addition, it is particularly preferable when the compression belt is affixed to the sole section. Such a fixation of the compression belt preferably in the area of the heel of a foot surrounded by the main body makes it easier to guide the compression belt when putting on the ankle brace, and a reproducible location for guidance is ensured in the area of the sole section.

The present invention will be explained below with reference to a drawing showing an exemplary embodiment.

DETAILED DESCRIPTION OF THE PREFERRED EMBODIMENT AND BEST MODE

Figure 1:
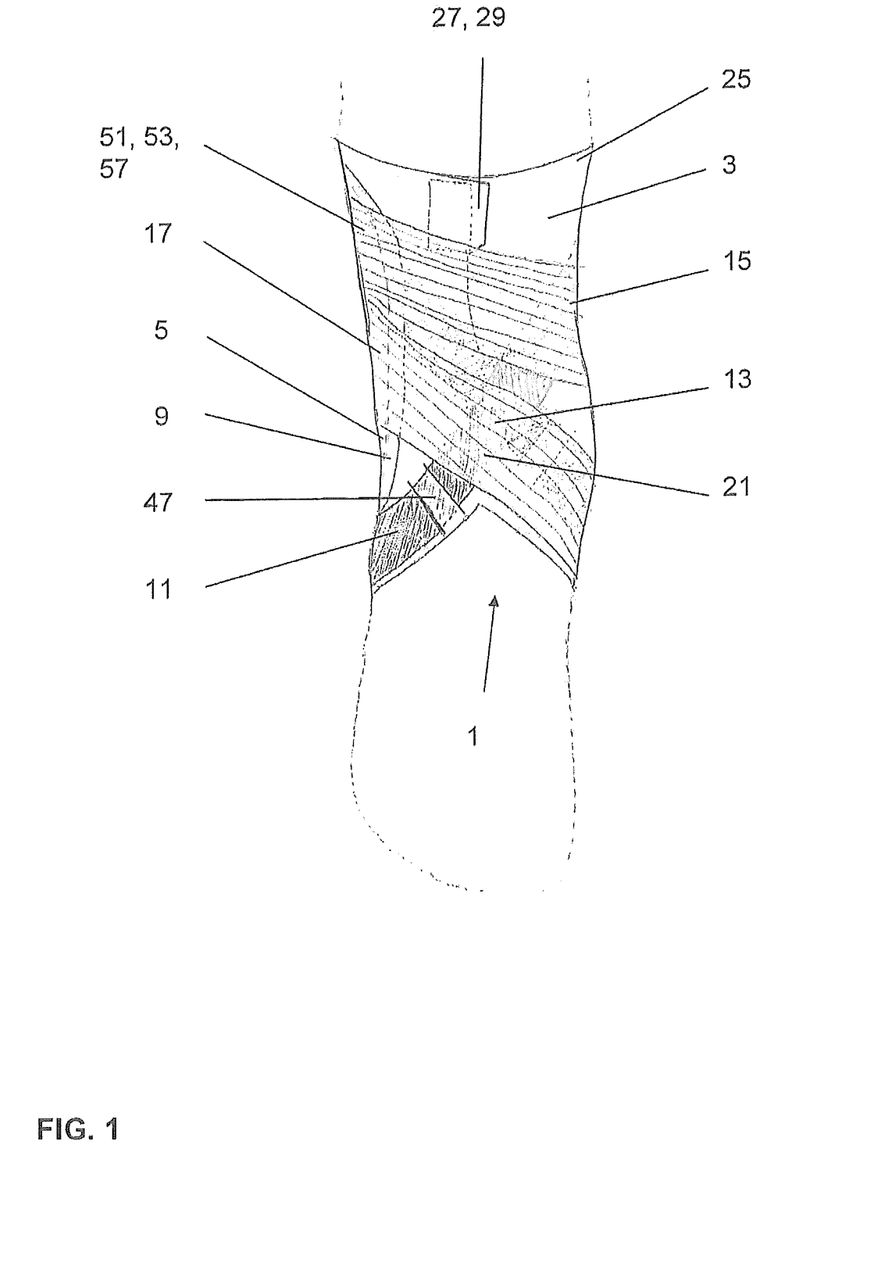
FIG. 1 shows an anterior view of an exemplary embodiment of an ankle brace according to the invention.

FIG. 1 shows an exemplary embodiment of an ankle brace 1 according to the invention that can be used in the present case to adjust the pronation of an ankle that it surrounds. The ankle brace 1 comprises a main body 3, a lateral and medial splint element 5, 7, an applied reinforcement 9, a fixing belt 11, and a compression belt 13.

Figure 2:
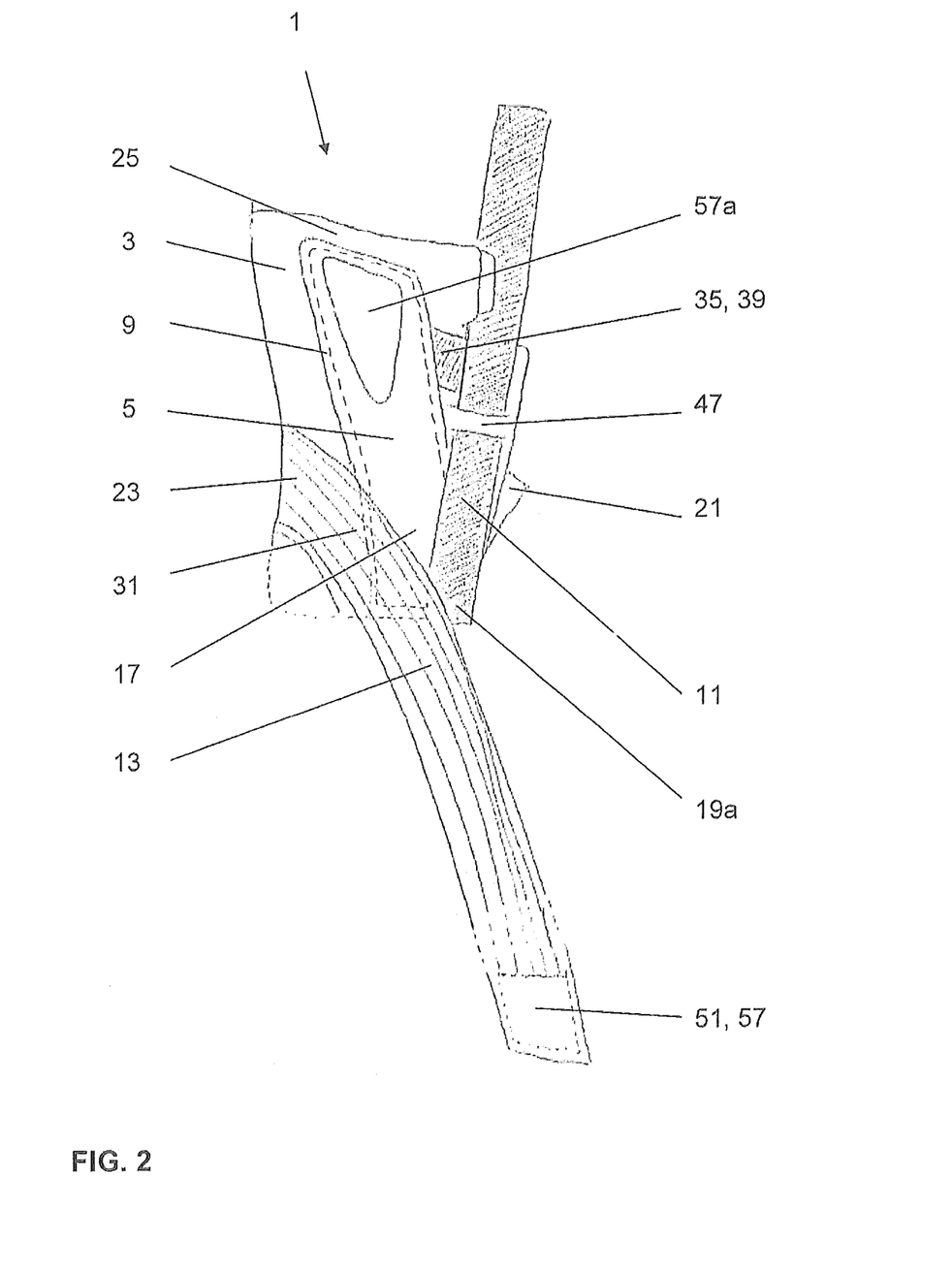
FIG. 2 shows a lateral view of the exemplary embodiment from FIG. 1.
Figure 3:
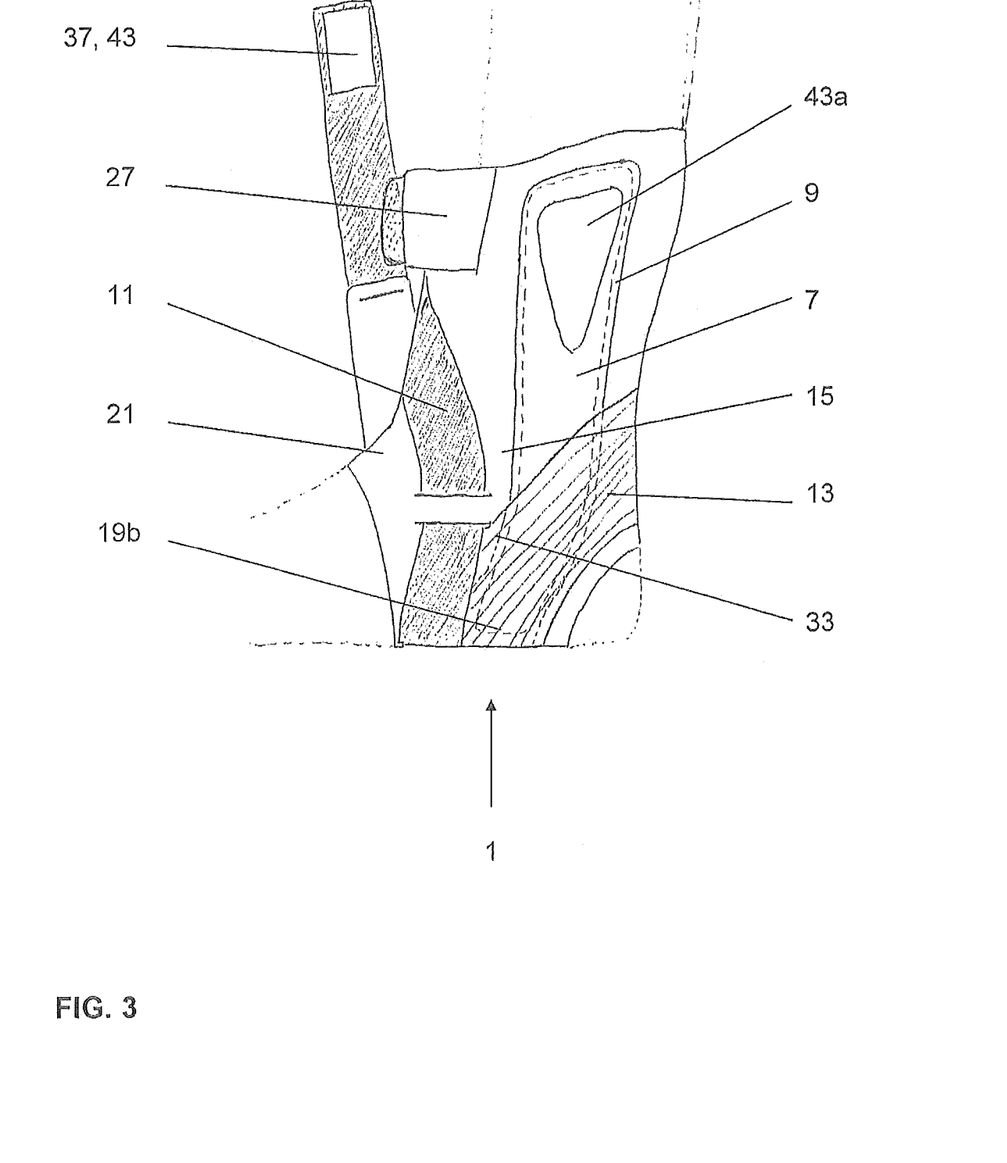
FIG. 3 shows a medial view of the exemplary embodiment from FIG. 1.
Figure 4:
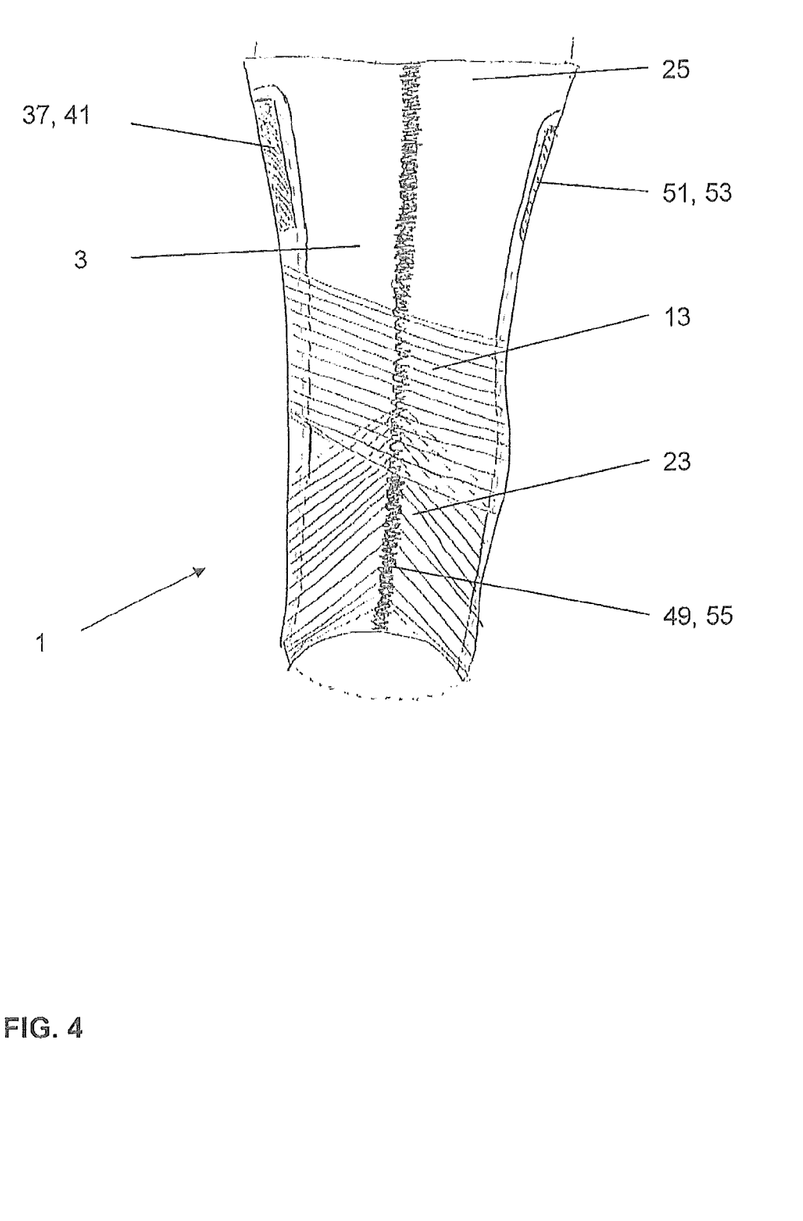
FIG. 4 shows a posterior view of the exemplary embodiment from FIG. 1.
Figure 5:
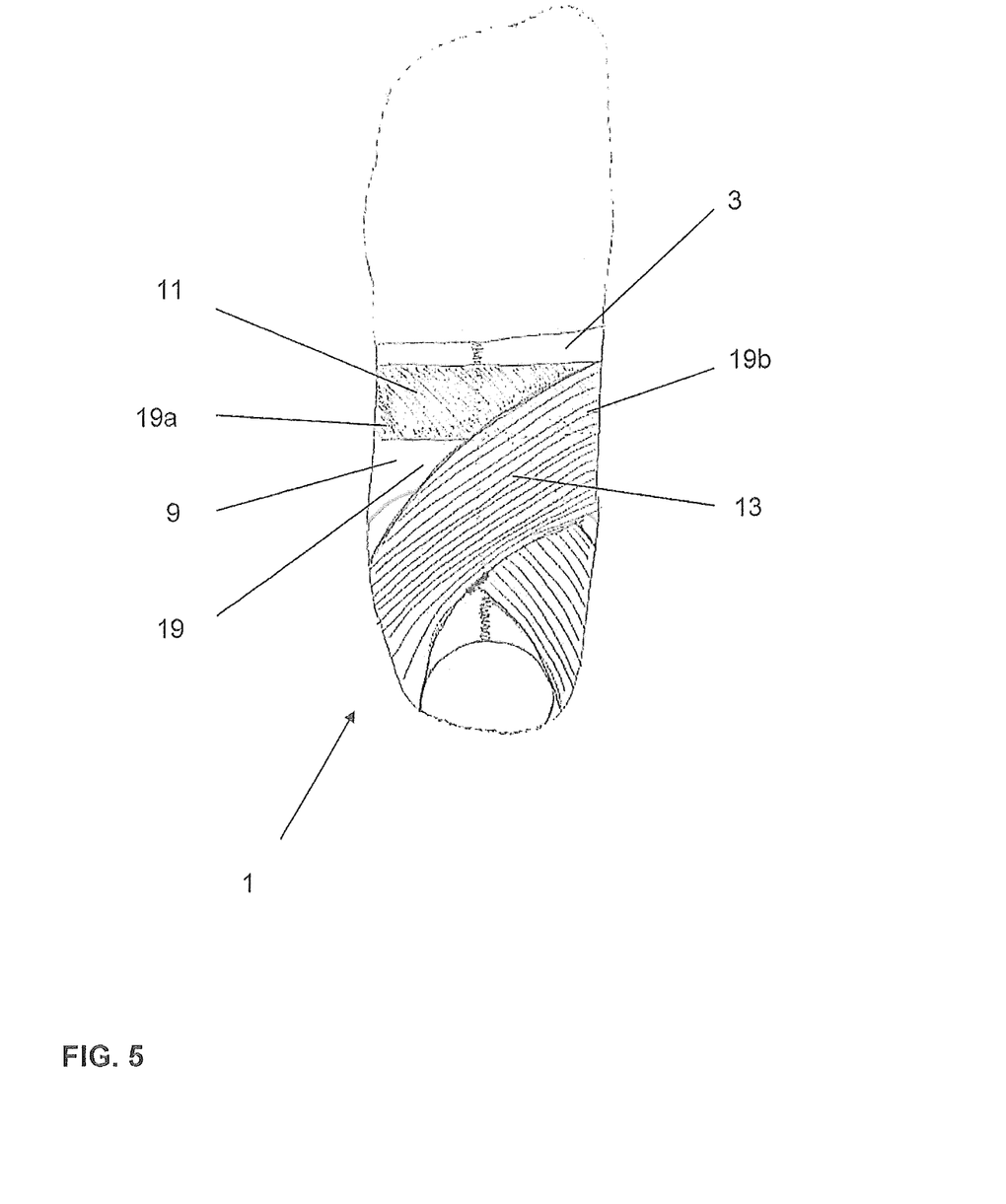
FIG. 5 shows a plantar view of the exemplary embodiment from FIG. 1.
Figure 6:
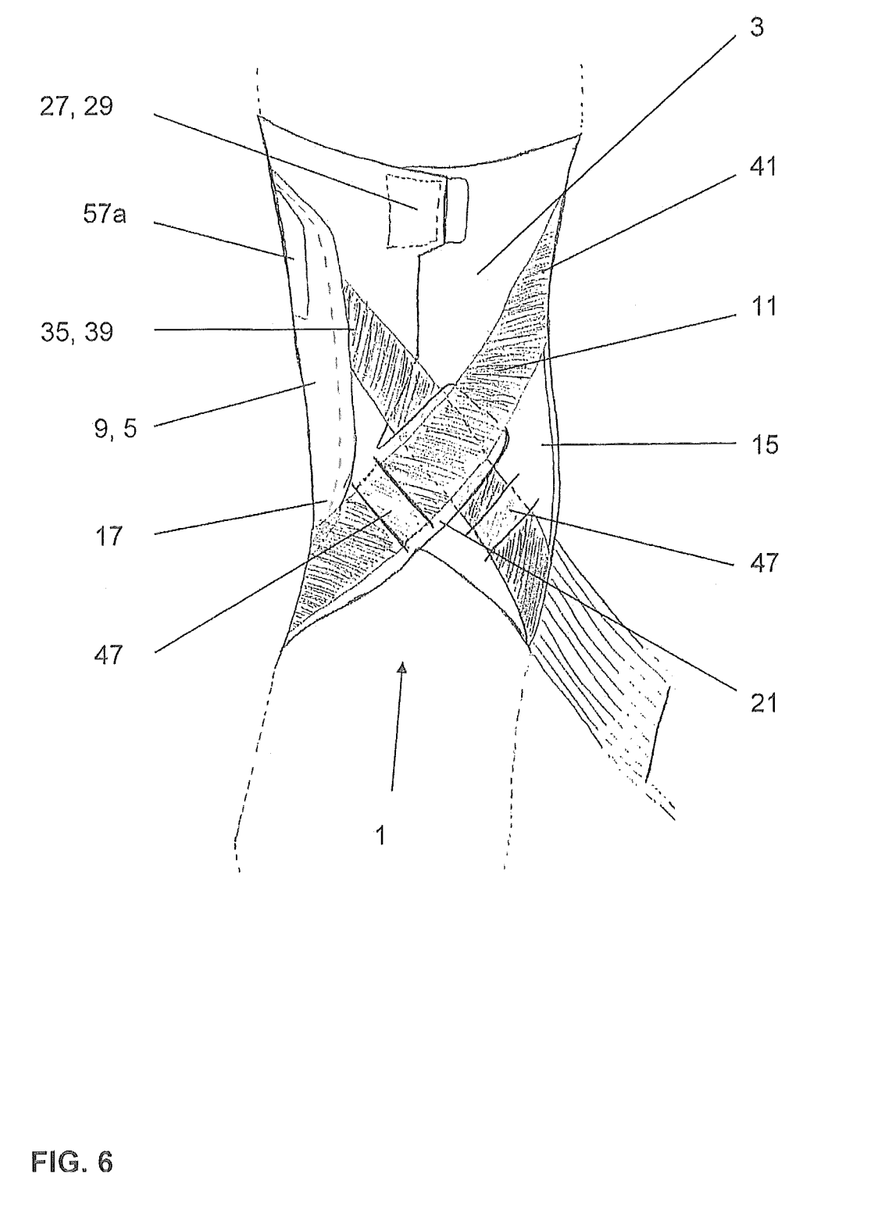
FIG. 6 shows a second anterior view of the exemplary embodiment from FIG. 1, with the compression belt being removed.

The main body 3 is formed from a flexible material to surround, i.e., closely lie against a human leg in the area of the ankle joint from the lower leg to the midfoot. The main body 3 has a medial section 15 (see FIG. 3), a lateral section 17 (see FIG. 2), a sole section 19 (see FIG. 5) with a lateral and medial side 19a, 19b, an arch and instep section 21 (see FIGS. 1 and 6), and a posterior section 23 (see FIG. 4). The sections can be formed together as a single piece, or the main body 3 can have sections that are, for example, sewn together.

The medial section 15 is provided to contact the medial side, the lateral section 17 is provided to contact the lateral side, the sole section 19 is provided to contact the sole, the arch and instep section 21 is provided to contact the arch and/or instep, and the posterior section 23 is provided to contact the posterior side of a foot or a leg surrounded by the main body 3 in the area of the ankle joint from the lower leg to the midfoot.

The main body 3 has a top end 25 that adjoins the main body 3 surrounding the foot on the sides of the lower leg, i.e., at a distance from the sole section 19.

The main body 3 further has an opening section 27 that extends from the arch and instep section 21 to the top end 25 of the main body 3. The opening section 27 is formed by a tab 29 that is fixedly connected to the lateral section 17 of the main body 3, or is formed as a single part therewith.

To close the opening section 27, the tab 29 can be brought into contact with the medial section 15 of the main body 3 and be releasably connected thereto. To open the opening section 27, the tab 29 can be disconnected from the medial section 15 of the main body 3, and then the medial and lateral sections 15, 17 are separated from each other so that the main body 3 is opened up. The ankle brace 1 can thereby easily be put onto a foot.

However, it is alternately conceivable for the tab 29 to be fixedly connected to the medial section 15 and releasably connectable to the lateral section 17.

Figure 7:
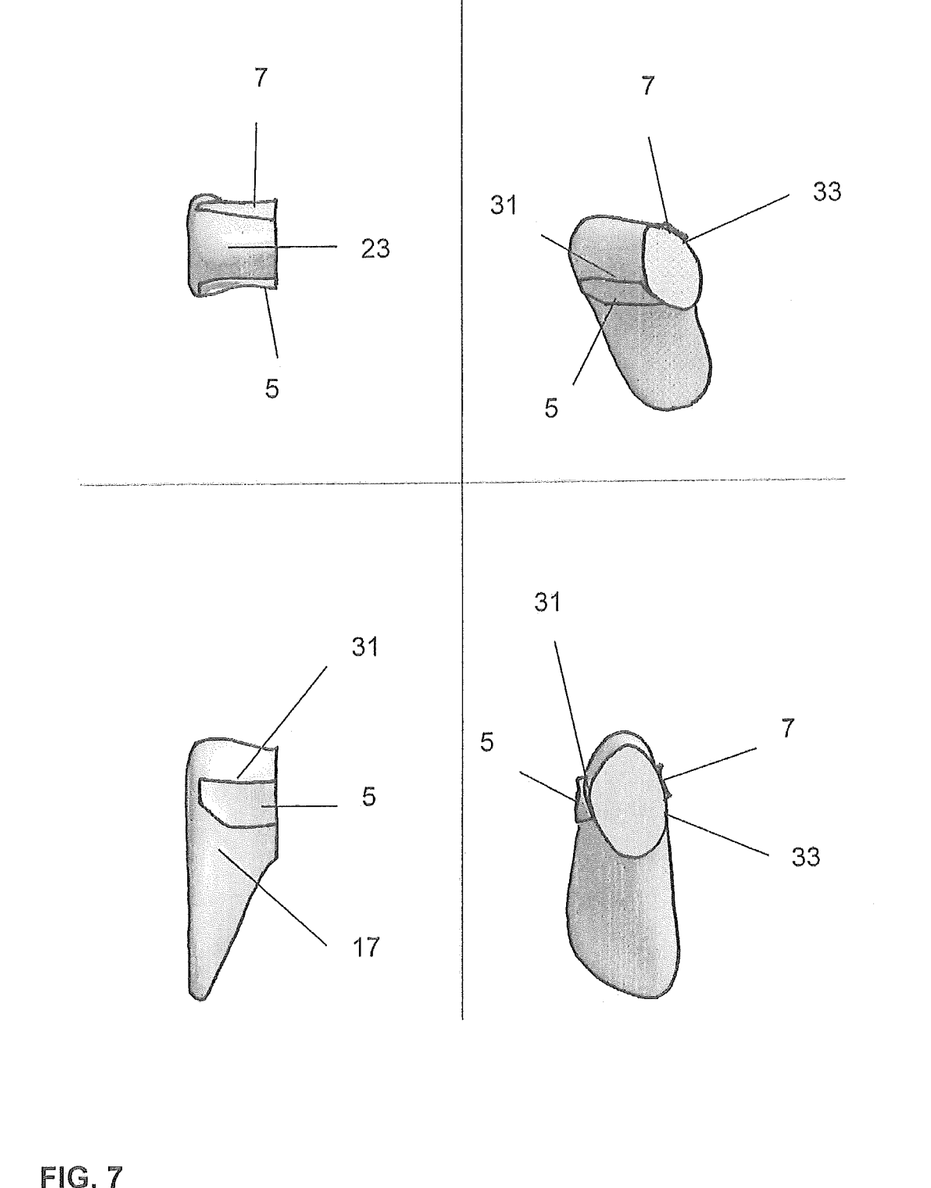
FIG. 7 shows four perspective views of the position of the splint elements of an exemplary embodiment of an ankle brace according to the invention relative to a foot that can be surrounded by the ankle brace.

The lateral and the medial splint elements 5, 7 are fixed to the lateral and medial sections 17, 15 of the main body 3 with the assistance of the applied reinforcement 9. The splint elements 5, 7 are arranged between the main body 3 and the applied reinforcement 9 and are held by the applied reinforcement 9 to the main body 3. The splint elements 5, 7 are formed from a rigid material and extend from the lateral or medial side 19a, 19b of the sole section 19 into the area of the lateral or medial section 17, 15, that adjoins the top end 25 of the main body 3. The lateral splint section 5 is arranged on the lateral section 17 of the main body 3 such that it proceeds offset from a lateral ankle section 31 away from the posterior section 23 of the main body 3 (see FIG. 7). At the same time, the medial splint section 7 is attached to the medial section 15 of the main body 3 such that it proceeds offset from the medial ankle section 33 toward the posterior section 23 of the main body 3. The lateral ankle section 31 of the main body 3 is provided to lie against the ankle on the lateral side of the foot. In addition, the medial ankle section 33 is provided to lie against the ankle on the medial side of the foot. This arrangement of splint elements 5, 7 relative to the foot of a user is shown in detail in FIG. 7, wherein the position of the sections of the main body that are not shown are indicated by reference numbers "17," "23," "31," and "33."

By means of the arrangement of the splint elements 5, 7 offset from the ankle sections, a so-called talus prolapse is prevented. The forward shifting of the ankle bone in reference to the surface of the tibia joint is counteracted, wherein force is exerted on the ankle bone by the offset position of the splint elements when the ankle bone shifts forward in reference to the surface of the tibia joint.

Additionally, with this arrangement of the splint elements 5, 7, they do not lie directly against the ankle of the user, which can otherwise cause pain when pressure is exerted on the splint elements 5, 7.

The applied reinforcement 9 is designed contiguously, that is, preferably as a single piece, and extends from the area of the lateral section 17 that adjoins the top end 25 of the main body 3, along the lateral section 17 of the main body 3 across the lateral splint element 5 to the lateral side 19a of the sole section 19, around the sole section 19 to the medial side 19b of the sole section 19, and along the medial section 15 of the main body 3 across the medial splint element 7 to the area of the medial section 15 that adjoins the top end 25 of the main body 3. The applied reinforcement 9 is designed to be non-stretchable in this direction of extension of the applied reinforcement 9 from the top end 25 of the lateral section 17 across the sole section 19 to the top end 25 of the medial section 15 of the main body 3.

By means of this non-stretchable construction, the applied reinforcement 9 prevents the sole section 19 from expanding perpendicular to its longitudinal extension, and thereby ensures that the sides 19a, 19b of the sole section 19 always remain arranged at a specific position relative to the foot of the user.

A fixing belt 11 is also provided on the main body 3. The fixing belt 11 is formed from a high-strength material and has a first and second end 35, 37. The fixing belt 11 is preferably formed from a non-elastic material so that its length remains substantially unchangeable in the direction of extension. In the present exemplary embodiment, the first end 35 of the fixing belt 11 is fixedly connected to the area of the lateral section 17 of the main body 3 that adjoins the top end 25 of the main body 3.

It is, however, also conceivable for the first end 35 to be fixedly or releasably connected to the main body 3 in a preset position relative thereto, for example by a snap fastener connection. It is also conceivable for the user to be able to select one of a plurality of snap fasteners on the main body 3 to fasten the corresponding companion piece on the first end 35 of the fixing belt 11.

In each case, the position at which the first end 35 is connected to the main body 3 is set and not distributed over an area such as, for example, would be the case with a hook-and-loop fastener.

The second end 37 of the fixing belt 11 is releasably connected to the area of the medial section 15 of the main body 3 that adjoins the top end 25 of the main body 3.

The fixing belt 11 extends between the first and second end 35, 37 like a loop around the foot surrounded by the main body 3 in the area of the midfoot and is movable along its entire length relative to the main body 3. The first end 35 of the fixing belt 11 proceeds from its fixed attachment 39 to the main body 3 in the area of the lateral section 17 across the arch and instep section 21 toward the medial side 19b of the sole section 19 around the sole section 19 up to the lateral side 19a of the sole section 19, and from there across the arch and instep section 21 up to the location of the releasable attachment 41 of the second end 37 of the fixing belt 11 to the medial section 15 of the main body 3.

This releasable connection of the fixing belt 11 to the main body 3 is realized in the exemplary embodiment described here by a hook-and-loop fastener 43, preferably by a Velcro® connection. The location of the releasable connection 41 of the fixing belt 11 to the main body 3 in the present exemplary embodiment is on the applied reinforcement 9 in the medial section 15 of the main body 3.

In order to achieve pronation of the lateral side 19a of the sole section 19, the fixing belt 11 is tightened, wherein it can move along its entire length relative to the main body 3 due to the displaceability. To flexibly adapt the degree of pronation to which the foot is to be adjusted, the fixing belt 11 can be releasably attached at locations at different distances away from the lateral side 19a of the sole section 19, since the hook-and-loop fastener 43 has a certain amount of width on the applied reinforcement 9. The location of the releasable connection 41 of the fixing belt 11 on the main body 3 is flexibly adaptable or shiftable within a certain area of the medial section 15 adjacent the top end 25 of the main body 3 due to the large surface of the hook-and-loop fastener base 43a.

In order to guide the fixing belt 11 on the main body 3 or movably fix it along its direction of extension, guide tabs 47 are provided that are fixed to the main body 3 in the area of the arch and instep section 21.

To additionally compress the foot, another belt, the compression belt 13, is provided. This compression belt 13 has an elastic material and a mesh structure. The compression belt 13 also has a first end 49 and a second end 51, and can be wound around the main body 3, the fixing belt 11, and the applied reinforcement 9, wherein the first end 49 of the compression belt 13 is releasably attached either to the main body 3, the fixing belt 11, or the applied reinforcement 9. In the present exemplary embodiment, the first end 49 of the compression belt 13 is fixedly attached to the posterior section 23 of the main body 3, and the second end 51 of the compression belt 13 is releasably connected to the applied reinforcement 9 in the area of the lateral section 17 of the main body 3, which adjoins the top end 25 of the main body 3.

This releasable connection 53 of the compression belt 13 to the applied reinforcement 9 in the lateral section 17 of the main body 3 is also realized by a hook-and-loop fastener 57, preferably by a Velcro® connection. As is the case with the fixing belt 11, the location of the releasable attachment 53 of the compression belt 13 is flexible within a certain range of its direction of extension. The hook-and-loop fastener base 57a on the applied reinforcement 9 has a certain amount of width that enables the second end 51 of the compression belt 13 to be attachable at points spaced along its direction of extension.

The compression belt 13 is designed for its first end 49 to be guided from the place of fixed attachment 55 to the posterior section 23 of the main body 3 along the lateral side 19a of the sole section 19, around the sole section 19 to the medial side 19b of the sole section 19, across the arch and instep section 21 up to the lateral section 17, and from there in a spiral around the lower leg of the foot or leg surrounded by the main body 3 in a direction away from the side of the sole section 19, first around the posterior section 23, then around the medial section 15, and finally up to the area of the lateral section 17 that adjoins the top end 25 of the main body 3 to be releasably connected there to the applied reinforcement 9.

In order to simplify the guidance of the compression belt 13 in the area of the sole section 19 and to ensure a precise and reproducible seat of the compression belt 13 in this area, the compression belt 13 is fixed at the sole section 19, preferably at half the width of the sole section 19 between the lateral and medial side 19a, 19b adjacent the posterior section 23 of an enclosed foot.

By means of the flexible or shiftable attachment 53 of the second end 51 of the compression belt 13 to the main body 3 or the applied reinforcement 9 in the direction of extension of the compression belt 13, the pressure that is transmissible by the compression belt 13 to the main body 3, the applied reinforcement 9, and the fixing belt 11, which is basically transmitted evenly to the aforementioned structure underneath (main body 3, applied reinforcement 9, and fixing belt 11) and hence indirectly to the enclosed leg or enclosed foot, can be adapted as desired.

In addition, the above-described path of the compression belt 13 along the main body 3 evenly distributes the pressure applied by tightening the compression belt 13 to the structure underneath (main body 3, applied reinforcement 9, and fixing belt 11), and no pressure peaks arise that are unpleasant to the user or are orthopedically disadvantageous. The pressure exerted by the compression belt 13 causes it to assume an effect similar to a bandage and ensures that the splint elements 5, 7 arranged underneath very closely and rigidly lie against the lower leg bone, tendons, and ligaments and splint them.

The ankle brace 1 can be used as follows: The opening section 27 is first opened by undoing the tab 29 from the medial section 15 and expanding the main body 3, for example, with one's hands. Then a user inserts his/her foot into the main body 3 and subsequently closes the opening section 27 by applying the tab 29 to the medial section 15 and releasably fixing it thereto.

When putting on the ankle brace 1, the fixing belt 11 and compression belt 13 are preferably loosened, that is, their second end 37, 51 is removed from the main body 3 or the applied reinforcement 9. To achieve the effect of pronation of the foot enclosed by the main body 3, the user tightens the second end 37 of the fixing belt 11 and then releasably attaches the second end 37 by means of a hook-and-loop fastener 43a to the main body 3, or to the applied reinforcement 9, to achieve the desired degree of pronation, and the outside of the foot is lifted to the desired extent. The shiftability of the fixing belt 11 relative to the main body 3 ensures that the latter does not rotate, distort, or twist in relation to the user's foot, and that the overall foot is actually tilted as desired.

The user subsequently tightens the second end 51 of the compression belt 13 and adjusts to the desired degree of compression on the foot by releasably affixing the second end 51 of the compression belt 13 at a suitable place on the hook-and-loop fastener base 57a in the lateral section 17 of the main body 3 to the applied reinforcement 9.

Since the lateral and medial splint elements 5, 7 in the present exemplary embodiment are offset in the above-described manner in relation to the ankle sections 31, 33, pressure directed in a posterior direction is also exerted on the ankle bone.

The following three effects, among others, can be achieved by the present ankle brace 1:

By means of the fixing belt 11, pronation or supination of the foot held by the brace can be achieved depending on whether the first or second end 35, 37 of the fixing belt is releasably connected to the main body 3.

By means of the splint elements 5, 7, the lower leg or ankle is simultaneously splinted, and the position of the splint elements 5, 7 counteracts a talus prolapse.

The entire area of the ankle joint of a leg enclosed by the main body 3 is compressed from the lower leg to the midfoot by means of the compression belt 13.

While the invention has been described with reference to specific embodiments and examples, it is envisioned that various details of the invention may be changed without departing from the scope of the invention. Furthermore, the foregoing description of the preferred embodiments of the invention and best mode for practicing the invention are provided for the purpose of illustration only and not for the purpose of limitation.

We claim:

1. An ankle brace for adjusting ankle pronation and supination comprising:
    (a) a flexible main body adapted to surround an ankle and foot of a wearer, the flexible main body including a medial section configured to extend along an inner portion of the ankle, a lateral section opposite the medial section configured to extend along an outer portion of the ankle, and a sole, arch and instep sections configured to extend along the foot;
    (b) a first adjustable rigid splint element extending longitudinally throughout the medial section of the flexible main body and a second adjustable rigid splint element extending longitudinally throughout the lateral section of the flexible main body in which the first and second rigid splint elements are separated by the sole section;
    (c) an adjustable non-elastic fixing belt having a first end connected to an upper portion of the main body adjacent to at least one of the first and second adjustable rigid splint elements and being received through a guide tab on the flexible main body that is adjacent to at least one of the first and second adjustable rigid splint elements, the adjustable non-elastic fixing belt is configured to extend circumferentially around the flexible main body such that a first portion of the adjustable non-elastic fixing belt extends across an anterior portion of the main body, the fixing belt continues substantially perpendicular to the sole section and wraps around the anterior portion of the main body such that a second portion of the non-elastic fixing belt is configured to overlap the first portion of the non-elastic fixing belt and a second end of the fixing belt connects to the main body such that the adjustable non-elastic fixing belt is angled relative to the first and second rigid splint elements to provide selective tension and position of the first and second adjustable rigid splint elements thereby selectively adjusting ankle pronation and supination; and
    (d) an elastic belt fixed to the main body that is adapted to wrap around the flexible main body, first and second rigid splint elements, and fixing belt to secure selective tension and position of the first and second adjustable rigid splint elements.

2. The ankle brace of claim 1, further comprising reinforcing elements forming pockets extending longitudinally on the medial and lateral sections of the flexible body that receive the first and second adjustable rigid splint elements respectively.

3. The ankle brace according to claim 1, wherein one of the first end or the second end of the fixing belt is fixedly connected to the main body.

4. The ankle brace according to claim 1, wherein one of the first end or the second end of the fixing belt is releasably connected to the main body in a plurality of fixed positions relative to the main body.

5. The ankle brace according to claim 1, wherein one of the first end or the second end of the fixing belt is connected to the main body by one or more releasable connections at a preset position.

6. The ankle brace according to claim 5, wherein the other of the first end or the second end of the fixing belt is adapted to be releasably connected to the main body by a hook-and-loop connection.

7. The ankle brace according to claim 1, wherein the guide tab is positioned along the path of the fixing belt to movably guide the fixing belt.

8. The ankle brace according to claim 1, wherein an applied reinforcement element is provided contiguously on the main body, and extends from a top end of and across the lateral section, across the sole section, across the medial section up to a top end of the medial section.

9. The ankle brace according to claim 8, wherein the material of the applied reinforcement element is adapted to be non-stretchable in its path from the top end of the lateral section to the top end of the medial section.

10. The ankle brace according to claim 8, wherein the first and second splint elements are affixed between the main body and the applied reinforcement element.

11. The ankle brace according to claim 1, wherein the main body includes a posterior section adapted to lie on the posterior side of the foot, a lateral ankle section adapted to be positioned on the lateral side of the foot and ankle, and a medial ankle section adapted to be positioned on the medial side of the foot and ankle, whereby the second splint element on the lateral section of the main body extends in an offset direction away from the posterior section such that the second splint element extends across from the lateral ankle section toward the arch and instep section in an offset direction, and further wherein the first splint element on the medial section of the main body is arranged so as to be offset with respect to the posterior section such that the first splint element extends across from the medial ankle section toward the posterior section in an offset direction.

12. The ankle brace according to claim 1, wherein the elastic belt is affixed to the sole section.

\* \* \* \* \*